United States Patent [19]

Wiegers et al.

[11] Patent Number: 4,604,487

[45] Date of Patent: Aug. 5, 1986

[54] PROCESS FOR PREPARING PHENYL ALKANOL AND PERFUMERY USES OF RESULTING PRODUCT

[75] Inventors: Wilhelmus J. Wiegers, Red Bank; Mark A. Sprecker, Sea Bright, both of N.J.

[73] Assignee: International Flavors & Fragrances Inc., New York, N.Y.

[21] Appl. No.: 747,449

[22] Filed: Jun. 21, 1985

Related U.S. Application Data

[60] Division of Ser. No. 589,472, Mar. 14, 1984, Pat. No. 4,549,983, which is a continuation-in-part of Ser. No. 482,823, Apr. 7, 1983, Pat. No. 4,512,918.

[51] Int. Cl.[4] .......................................... C07C 33/18
[52] U.S. Cl. ................................ 568/715; 252/522 R
[58] Field of Search ................ 568/715, 761, 766; 252/522 R

[56] References Cited

U.S. PATENT DOCUMENTS

| 4,158,100 | 6/1979 | Sherwin | 568/715 |
| 4,486,607 | 12/1980 | Webb | 568/715 |
| 4,512,918 | 4/1985 | Wieger et al. | 252/522 R |
| 4,549,983 | 10/1985 | Wieger et al. | 252/522 R |

FOREIGN PATENT DOCUMENTS 433121 8/1975 U.S.S.R. ............................ 568/715

*Primary Examiner*—Werren B. Lone
*Attorney, Agent, or Firm*—Arthur L. Liberman

[57] ABSTRACT

Described is a method for producing the substantially pure compound defined according to the structure:

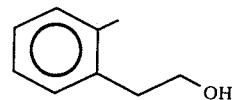

and uses thereof in augmenting or enhancing the aroma of perfume compositions, colognes and perfumed articles such as perfumed polymers and solid or liquid anionic, cationic, nonionic or zwitterionic detergents, fabric softener compositions and fabric softener articles. Also described are processes and compositions for use in perfume aroma augmenting, enhancing, modifying and altering compositions and as perfume, cologne and perfumed article aroma imparting compositions of mixtures of the compound having the structure:

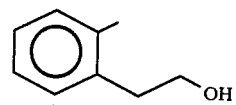

taken further together with one or more butanolyl cyclohexane derivatives and/or 3-methyl-1-phenyl-pentanol-5.

The process for preparing the compound having the structure:

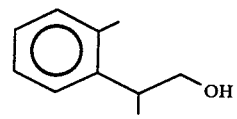

involves a one-step reaction wherein the compound having the structure:

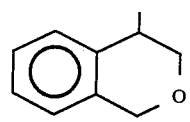

is hydrogenated in the presence of acid.

3 Claims, 4 Drawing Figures

GLC PROFILE FOR EXAMPLE I. CRUDE

GLC PROFILE FOR EXAMPLE I.
CRUDE

GLC PROFILE FOR EXAMPLE I.
CRUDE

NMR SPECTRUM FOR FRACTION 12 OF EXAMPLE I.

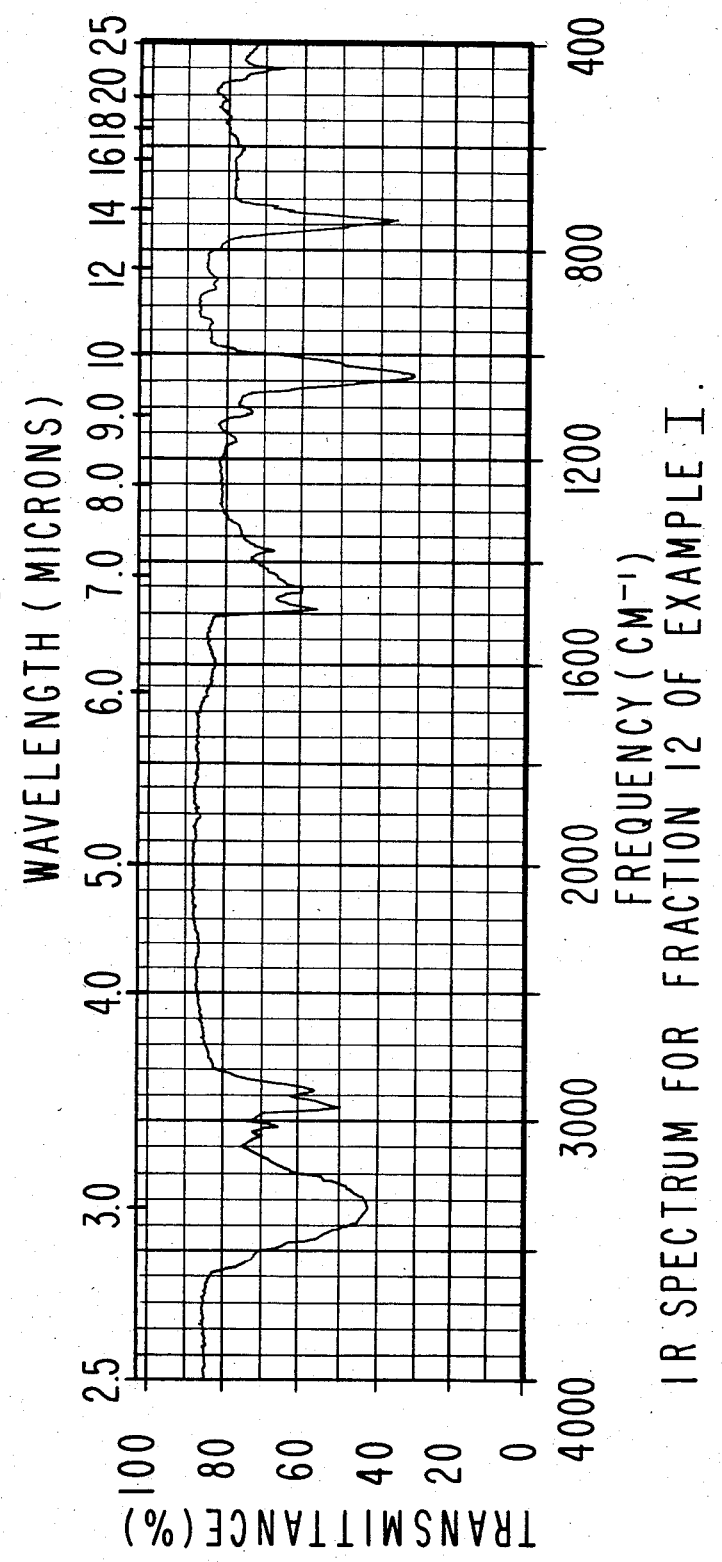

PROCESS FOR PREPARING PHENYL ALKANOL AND PERFUMERY USES OF RESULTING PRODUCT

This is a divisional of application Ser. No. 589,472, filed 3/14/84 now U.S. Pat. No. 4,549,983 which, in turn, is a continuation-in-part application for Ser. No. 482,823 filed on 4/7/83 now U.S. Pat. No. 4,512,918 issued 4/23/85.

BACKGROUND OF THE INVENTION

The present invention relates to the use in augmenting, enhancing or modifying the aroma of perfume compositions, colognes and perfumed articles of the substantially pure compound having the structure:

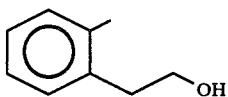

taken alone or taken further together with butanoyl cyclohexane derivatives defined according to the structure:

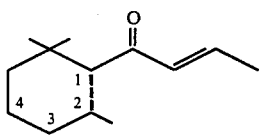

wherein one of the dashed lines is a carbon-carbon double bond or two of the dashed lines are carbon-carbon double bonds (but that when two of the dashed lines represent carbon-carbon double bonds, the carbon-carbon double bonds are conjugated), and/or 3-methyl-1-phenyl-pentanol-5 having the structure:

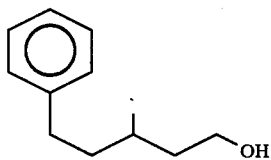

The present invention also relates to a process for preparing the substantially pure compound having the structure:

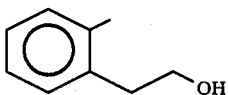

by means of reacting the compound having the structure:

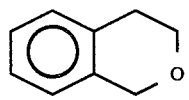

with hydrogen in the presence of acid.

There has been considerable work performed relating to substances which can be used to impart (or alter, modify or enhance) fragrances to (or in) perfume compositions, colognes or perfumed articles such as solid or liquid anionic, cationic, nonionic or zwitterionic detergents, fabric softener compositions and fabric softener articles as well as perfumed polymers. These substances are used to diminish the use of natural materials some of which may be in short supply and/or to provide more uniform properties to the finished product.

Strong rosy, carnation, leafy and green aromas with balsamic and cedarwood top notes are highly desirable in many types of perfume compositions, perfumes and perfumed articles.

Phenylethyl alcohol having the structure:

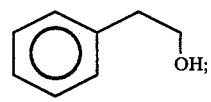

tolitol having the structure:

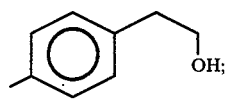

and hydratropic alcohol having the structure:

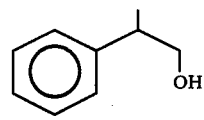

are well known aryl alkanols having uses in augmenting or enhancing rose aromas in perfume compositions, colognes and perfumed articles. Furthermore, a highly impure form of the compound having the structure:

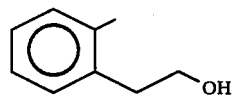

is disclosed as having perfume uses.

Reference is made to the monographs concerning these compounds in the text Arctander, "Perfume and Flavor Chemicals (Aroma Chemicals)", Volumes I and II, to wit:

2513: PHENYLMETHYL ALCOHOL

Phenethylalcohol.
beta-Phenylethanol.
$1^2$-Oxy-1-ethylbenzol.
Benzyl carbinol.
beta-Hydroxy ethylbenzene.
2-Phenylethylalcohol.
Mellol (Bush-Boake-Allen).
Gallicol (Firmenich).
Phenarose (I.F. & F.).
Phenethylol.
P.E.A.

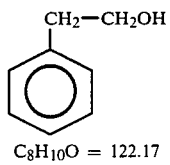

$C_8H_{10}O = 122.17$

Colorless oily liquid. Sp.Gr. 1.03. B.P. 220° C.

2% soluble in water, except for commercial grade which may be only 1.5% soluble. Soluble in Propylene glycol, miscible with alcohol and oils.

Mild and warm, Rose-honey-like odor of moderate to poor tenacity. Poorer grades show earthy or pungent, more Hyacinth-like topnotes, or greener "gassy" notes. Very sensitive evaluation can be undertaken by smelling the aqueous solution. Most impurities are insoluble in water and will show up many times stronger, while the pure alcohol only smells mild, rosy in water.

Water is soluble in Phenylethylalcohol at the rate of 9%.

The alcohol has a measurable bactericidal effect at concentrations higher than 0.5% (in water).

The taste of this alcohol is sweet and Honey-rose-like at concentrations lower than 40 ppm, but tends to become unpleasantly perfumey at higher concentrations.

Phenylethylalcohol is one of the most widely used of all perfume chemicals. The annual production in the United States of America is now over 2 Million pounds, although only one manufacturer is making the alcohol on a continuous scale.

This material enters perfume compositions at the rate of 5–10–20% or sometimes much more. Its low cost, versatility and general acceptability on odor, its excellent stability are factors speaking strongly in favor of this otherwise relatively weak odorant. However, its odor is clearly demonstrated in an experiment with an apparently weak crystalline fixative/odorant, such as Trichloro methyl phenyl carbinyl acetate (Trirosol, Rosetone, etc.). With 5% of the crystalline material, Phenylethylalcohol will smell not only much more rosy, it will last much longer, and its "rough" topnotes are pleasantly subdued, it has "three dimensions" instead of two.

But it is in the "everyday" perfumery that the subject alcohol is most appreciated. It is almost never "out of place" in a composition, be it floral, balsamic, Oriental, mossy, herbaceous or "modern-aldehydic". It is an inevitable companion to the "rose alcohols", Citronellol, Geraniol, Nerol, Dimethyloctanol, etc. and it may receive fixation from Guaiacwood oil, Nitromusks, Coumarin and Heliotropine, Rosetone, Resinoids, etc. It blends excellently with the Linalool family, and with all the newer "Lily"-alcohols, "Muguet"-alcohols, etc. as well as in Lime and Spice blends.

The title alcohol finds some use in flavor compositions, mainly in imitation Butter, Strawberry, Raspberry (very common ingredient), Caramel, Honey, Melon, and in various fruit complexes, etc.

The concentration used is normally low, about 0.1 up to 20 ppm, but most often near 1–3 ppm.

G.R.A.S. F.E.M.A. No.2858.

Prod.:

(1) from Styrene oxide by hydration.
(2) from Ethylene oxide and Benzene with Aluminium chloride.

Many other methods are in use, but method No. 1) may—with certain modifications—become the modern and future method for large-scale production.

26-654; 64-499; 100-792; 106-293; 140-130; 156-306; 160-1152; 163-62; 163-232; 163-371; B-VI-478;

2190: ortho-METHYL PHENYLETHYL ALCOHOL ortho-2-Tolyl ethan-1-ol.

This material also forms part of commercial products called aryl-Methyl phenylethyl alcohol.

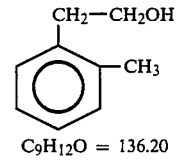

$C_9H_{12}O = 136.20$

Colorless oily liquid. B.P. 219° C.

Almost insoluble in water, soluble in alcohol and oils.

Sweet and mild, floral odor of Lilac-Rose type. Moderate to poor tenacity. Samples of different origin have shown considerable variation in odor characteristics. This may be due to the fact that commercial products almost inevitably contain meta-isomer, probably also para-isomer.

The subject alcohol finds some use in perfume compositions as a base for inexpensive Lilac, Rose, Honeysuckle and other floral fragrance types, and in Fougéres, Chypres, etc. It gives modifying notes to a Hyacinth and blends very well with all the Cinnamic derivatives.

Prod.: from ortho-Tolyl magnesium bromide plus Ethylene chlorhydrin.

68–500;

1707: HYDRATROPYL ALCOHOL

Hydratropic alcohol.
alpha-Methyl phenylethyl alcohol.
2-Phenyl propan-1-ol.
alpha-Phenylpropyl alcohol.
NOTE: This material is sometimes called:
beta-Phenylpropyl alcohol.

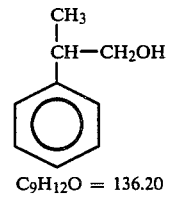

$C_9H_{12}O = 136.20$

Colorless liquid. B.P. 219° C. Sp.Gr. 1.02.

Slightly soluble in water, soluble in alcohol and Propylene glycol, miscible with oils.

Sweet-floral, but rather heavy odor of Lilac-Hyacinth type. Commercial products are rarely of high olfactory purity and may show variable amounts of harsh or "gassy" or Acetophenone-like topnotes which partly or wholly ruin the overall odor impression. This may also be the reason why perfumers generally do not even carry this material on their shelf—a simple objection to the material as it was first presented to them. Truly, an olfactorily pure grade of Hydratropyl alcohol shows quite interesting odor and should give the creative perfumer many good ideas.

It blends well with the "rose alcohols", with Eugenols and woody odors, with Oakmoss products and Vetiver, etc. With suitable blending in Cinnamic alcohol and derivatives, it may form background for Hyacinth and other floral bases.

This alcohol is occasionally used in flavor compositions, usually as a trace component in Berry, Melon, Honey and Nut compositions, or in rare floral flavor types. Its taste is rather heavy-sweet, woody-floral, but pleasant in concentrations below 20 ppm. Common use level is 0.5 to 1.5 ppm.

G.R.A.S. F.E.M.A. No.2732.

Prod.: (many methods), e.g.: by hydration of alpha-Methyl styrene.

4-63; 34-582; 68-501; 86-61;

It is to be emphasized that Arctander at Monograph 2190 states that the material defined according to the structure:

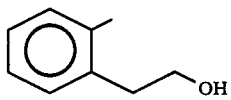

inevitably contains "meta-isomer" and "probably also para-isomer" and is produced from ortho-Tolyl magnesium bromoide plus Ethylene chlorhydrin, e.g., according to the reaction:

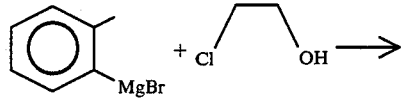

Arctander however, does not disclose the unexpected, unobvious and advantageous effects of the substantially pure compound having the structure:

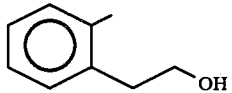

which is made by our novel process.

The compound defined according to the structure:

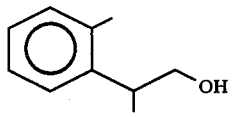

is known but its use in perfumery has heretofore been unknown. The synthesis of the compound having the structure:

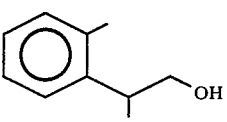

was heretofore known by means of a complex and cumbersome reduction of the corresponding carboxylic acid according to the reaction:

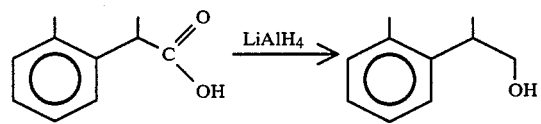

(Kusowkow, Zh. Obshch. Chim. 28 [1958] 2283,6).

U.S. Pat. No. 4,210,554 discloses fragrance compositions containing 3-methyl-1-phenyl-pentanol-5 or specific optical isomers thereof and one or more butanoyl cyclohexane derivatives. It is indicated in U.S. Pat. No. 4,210,554 that woody, rosy, green and earthy notes are desirable and augmented or enhanced in many types of perfume compositions, perfumes and perfumed articles by 3-methyl-1-phenyl-pentanol-5 and one or more butanoyl cyclohexane derivatives defined according to the structure:

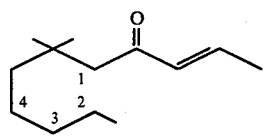

wherein one of the dashed lines is a carbon-carbon double bond or two of the dashed lines are carbon-carbon double bonds but when two of the dashed lines represent carbon-carbon double bonds, the carbon-carbon double bonds are conjugated.

U.S. Pat. No. 4,028,279 entitled "Novel Fragrance Composition Containing 2,6,6-Trimethyl-1-Cyclohexene-1-yl Acetaldehyde and Phenyl $C_6$ Ketone" relates to mixtures of (i) either or both of the phenyl $C_6$ ketones, 2,5-phenylhexen-1-one-3 and (ii) 2,2,6-trimethyl-1-cyclohexen-1-yl acetaldehyde used to alter, modify, enhance or impart aromas in or to perfumes, perfume compositions and/or perfumed articles. It is disclosed in said U.S. Pat. No. 4,028,279 that such perfume compositions containing such mixtures have intense rosy aromas with woody, green and earthy notes. The structure of the phenyl $C_6$ ketones disclosed in U.S. Pat. No. 4,028,279 is:

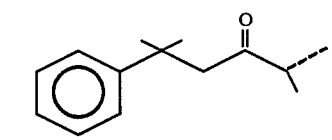

the structure of the betacyclohomocitral used in U.S. Pat. No. 4,028,279 is:

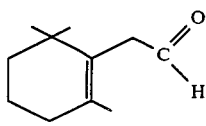

wherein the dashed line may be either a carbon-carbon single bond or a carbon-carbon double bond.

In U.S. Pat. No. 3,595,508, issued on May 25, 1976, mixtures of (i) 2,2,6-trimethyl-1-cyclohexen-1-yl acetaldehyde and (ii) 2,6,6-trimethyl crotonyl-1,3-cyclohexadiene having the structure:

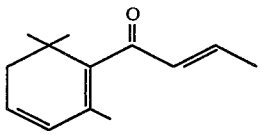

are indicated to produce in perfumes rosy, woody, camphoraceous, green and earthy notes.

Thus, nothing in the prior art including U.S. Pat. Nos. 4,210,554, 3,959,508 and 4,028,279 imply or state that such mixtures as are disclosed and claimed in the instant case can be used to enhance and extend specific rosy, carnation, leafy and green aromas with balsamic and cedarwood topnotes. Nothing in the prior art discloses a process for producing the substantially pure compound defined according to the structure:

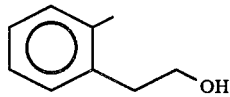

according to the reaction:

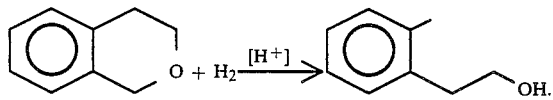

Nothing in the prior art discloses the unexpected, unobvious and advantageous perfumery properties of the substantially pure compound having the structure:

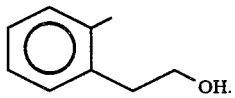

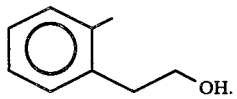

Figure 2:
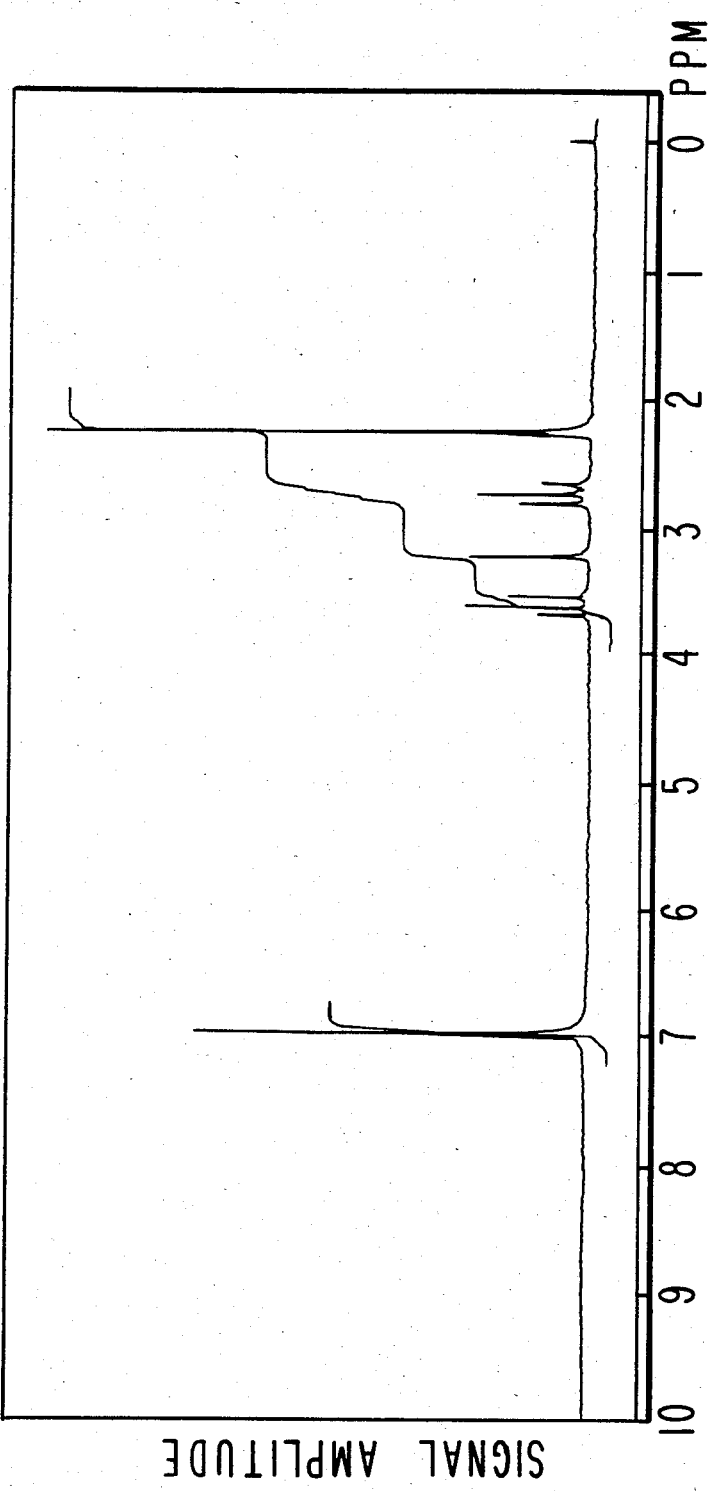

FIG. 2 is the NMR spectrum for Fraction 12 of the distillation product of the reaction product of Example I containing substantially pure compound having the structure:

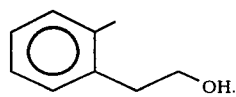

FIG. 3 is the infra-red spectrum for Fraction 12 of the distillation product of the reaction product of Example I containing substantially pure compound having the structure:

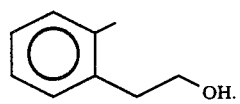

Figure 4:
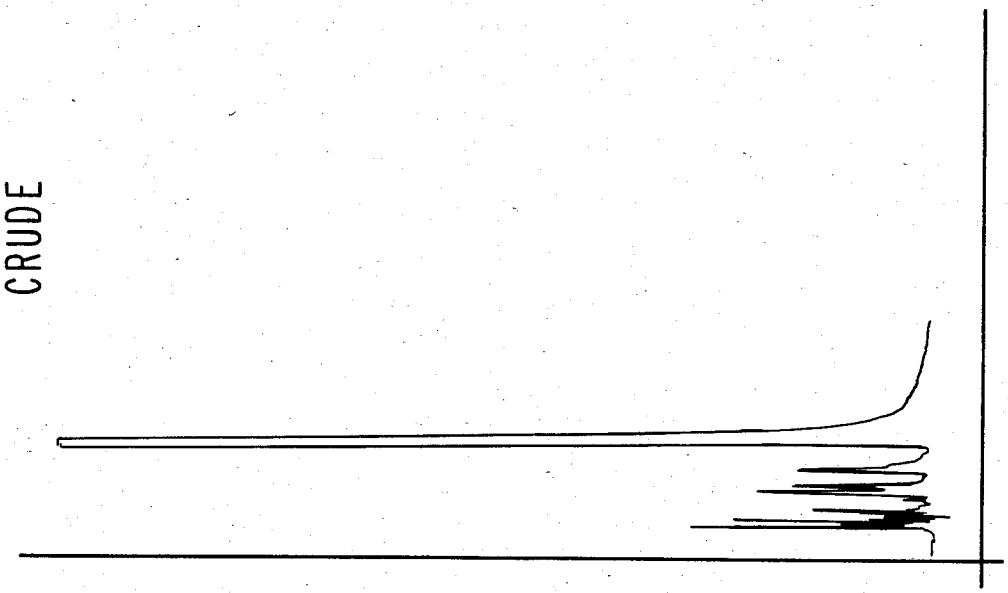

FIG. 4 is the GLC profile for the crude reaction product of Example II containing the compound having the structure:

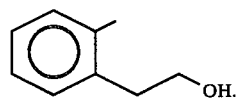

THE INVENTION

It has now been discovered that novel perfume compositions and perfumed articles as well as colognes having extended long-lasting, highly intense natural rose, carnation-like, leafy and green aromas with balsamic and cedarwood topnotes may be provided by the utilization of the substantially pure compound defined according to the structure:

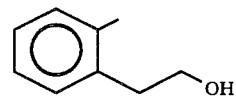

as well as by utilization of mixtures of the substantially pure compound having the structure:

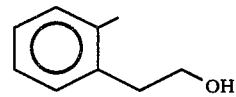

and (i) one or more butanoyl cyclohexane derivatives having the structure:

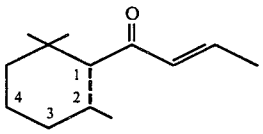

where one or two of the dashed lines is a carbon-carbon double bond and the other of the dashed lines are carbon-carbon single bonds with the proviso that if two of the dashed lines are carbon-carbon double bonds, the carbon-carbon double bonds are conjugated and/or (ii)

3-methyl-1-phenyl-pentanol-5 racemic mixtures or individual stereoisomers having one of the structures:

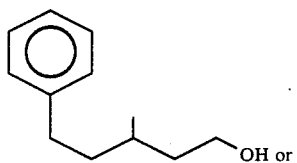

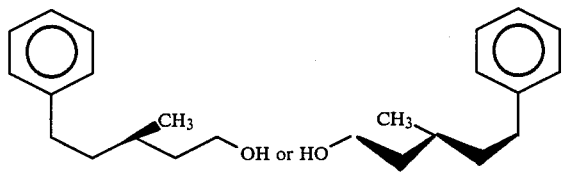

It has also been discovered that the substantially pure compound defined according to the structure:

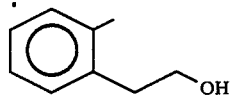

may be prepared by a highly cost effective process, specifically by means of reacting the compound having the structure:

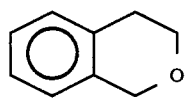

with hydrogen in the presence of acid according to the reaction:

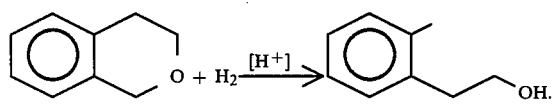

In carrying out the foregoing reaction various hydrogenation catalysts may be used, for example, palladium, platinum, and palladium-on-carbon, for example 3% up to 20% palladium-on-carbon. The reaction is carried out in the presence of a catalytic quantity of mineral acid, for example, phosphoric acid, sulfuric acid, hydrochloric acid and paratoluenesulfonic and methanesulfonic acid.

In place of the mineral acid, another acid may be used having a relatively high ionization constant such as citric acid.

The reaction temperature may be in the range from about 25° C. up to about 170° C. The reaction pressure is in the range of from about 50 psig up to about 1000 psig. The weight ratio of hydrogenation catalyst, e.g., palladium-on-carbon:acid, e.g., mineral acid such as phosphoric acid or other acids such as citric acid may vary from about 0.1:1 up to about 1:0.1 with a preferred weight ratio of about 1:1.

The hydrogenation reaction preferably takes place in the presence of a solvent which is inert to the reactants, for example, isopropyl alcohol, n-propyl alcohol, ethanol, benzene or toluene where a mineral acid is used.

When such acids as citric acid are used however, a presence of a solvent is not desirable.

At the end of the reaction, the reaction mass is filtered, stripped of solvent (if present) and distilled as by fractional distillation.

In perfumes, perfumed articles such as soaps and detergents (solid or liquid anionic, cationic, nonionic or zwitterionic detergents), optical brightener compositions, fabric softeners (for example, fabric softener compositions for clothes dryers), perfume compositions, colognes and perfumed polymers, it has been discovered by us that rose, carnation, leafy and green aromas with balsamic and cedarwood topnotes may be augmented or enhanced using the substantially pure compound having the structure:

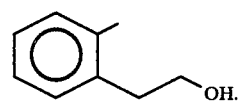

It has been further discovered by us that the organoleptic effect obtained when using mixtures containing (i) the substantially pure compound having the structure:

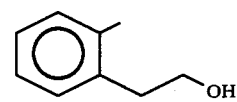

taken further together with (ii) 3-methyl-1-phenyl-pentanol-5 and/or one or more butanoyl cyclohexane derivatives is more than merely additive of the individual organoleptic properties of the compound having the structure:

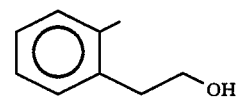

taken alone or taken further together with 3-methyl-1-phenyl-pentanol-5 and/or the butanoyl cyclohexane derivatives having the structure:

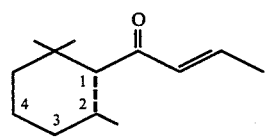

taken alone; and that the additive effect of the compound having the structure:

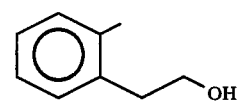

taken together with 3-methyl-1-phenyl-pentanol-5 and/or one or more butanoyl cyclohexane derivatives having the structure:

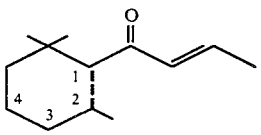

may be described as synergistic.

The 3-methyl-1-phenyl-pentanol-5 having one of the structures:

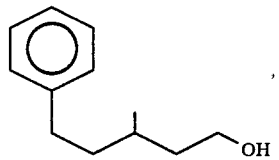

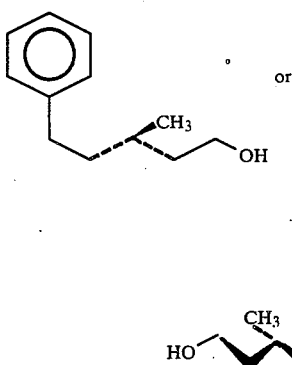

may be prepared according to the procedure described by Rupe Hirschmann and Werdenberg at Helv. Chimica Acta. 18 [1935] at pages 535-42 (abstracted at Beilstein E III 6; 1977, H 6, 551).

Methods for preparing the butanoyl cyclohexane derivatives which may be used in our invention are described in Swiss Pat. No. 520,479 issued on May 12, 1972 as well as in application for U.S. Pat. Ser. No. 851,727 filed on Nov. 15, 1977, now U.S. Pat. No. 4,211,242.

Contemplated within the scope of our invention are mole ratios of compound having the structure:

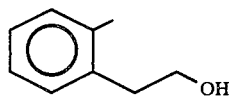

:butanoyl cyclohexane derivative having the generic structure:

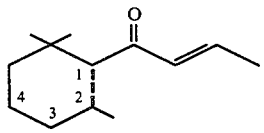

and/or 3-methyl-1-phenyl-pentanol-5 of from about 0.01:1 up to about 1:1 (mole ratio). It is however preferable in the practice of our invention to use mole ratio of compound having the structure:

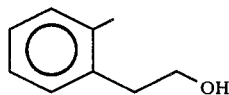

:butanoyl cyclohexane derivative and/or 3-methyl-1-phenyl-pentanol-5 derivative of from about 0.1:1 up to about 0.2:1.

When the compound having the structure:

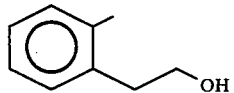

or mixtures of compounds having the structure: and 3-methyl-1-phenyl-pentanol-5 and/or one or more butanoyl cyclohexane derivatives of our invention (hereinafter referred to as phenyl alkanol-containing composition of matter) are used as perfume aroma adjuvants, the nature of the co-ingredients included with said phenyl alkanol-containing composition of matter in formulating the product composition will also serve to alter the organoleptic characteristics of any ultimate perfumed article treated therewith.

As used herein, the terms "alter" and "modify" in their various forms mean supplying or imparting a perfume aroma character or note to otherwise bland substances or augmenting the existing aroma characteristic where a natural aroma is deficient in some regard or supplementing the existing aroma impression to modify its quality, character or aroma.

As used herein, the term "enhance" is intended to mean the intensification (without effecting a change in the kind or quality of aroma) of one or more aroma nuances and their organoleptic impression of a perfume, perfume composition, cologne or one or more perfumed articles.

The phenyl alkanol-containing composition of matter of our invention and one or more auxiliary perfume ingredients, including, for example, alcohols (other than the 3-methyl-1-phenyl-pentanol-5 or compound having the structure:

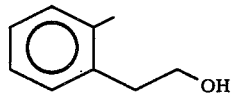

of our invention), aldehydes, ketones other than the butanoyl cyclohexane derivatives of our invention, nitriles, esters, lactones, natural essential oils and synthetic essential oils may be admixed so that the combined odors of the individual components produce a pleasant and desired fragrance particularly and preferably in the rose, carnation, leafy and green fragrance areas. It is to be understood that such additional adjuvants are to be organoleptically compatible with the compound having the structure:

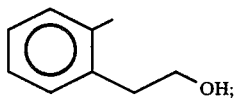

said 3-methyl-1-phenyl-pentanol-5 and one or more of said butanoyl cyclohexane derivatives of our invention and further that such adjuvants are to be non-reactive under use conditions at room temperature and storage conditions with the said compound having the structure:

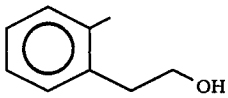

and with the said 3-methyl-1-phenyl-pentanol-5 and the butanoyl cyclohexane derivatives of our invention.

Such perfume compositions usually contain (a) the main note or the bouquet or foundation stone of the compositions, (b) modifiers which round off and accompany the main note, (c) fixatives which include odorous substances which lend a particular note to the perfume throughout all stages of evaporation and substances which retard evaporation and (d) topnotes which are usually low-boiling, fresh-smelling materials.

In perfume compositions, it is the individual components which will contribute their particular characteristics; and these individual components will also alter, modify or enhance the overall effect of the perfume composition. Thus the phenyl alkanol-containing composition of matter of our invention can be used to alter, augment or enhance the aroma characteristics of a perfume composition, for example, by utilizing or modifying the olfactory reaction contributed by one or more other ingredients in the composition.

The amount of phenyl alkanol-containing composition of matter of our invention which will be effective in perfume compositions depends upon many factors including the other ingredients, their amounts and the effects which are desired. It has been found that perfume compositions containing as little as 0.005% the phenyl alkanol-containing composition of matter of our invention and even less (e.g. 0.002%) can be used to impart a rose, carnation, leafy and green aroma with balsamic and cedarwood topnotes to cosmetics and other products including fabric softener articles used in clothes driers as well as in detergents and perfumed polymers. The amount employed can range up to 10% of the fragrance components and will depend on considerations of cost, nature of the end product, the effect desired on the finished product and the particular fragrance sought.

The phenyl alkanol-containing compositions of matter of our invention are useful taken alone or in perfume compositions as an olfactory component in anionic, cationic, nonionic and zwitterionic detergents and soaps, space odorants and deodorants, perfumes, colognes, toilet water, bath preparations such as bath oils and bath solids; hair preparations such as lacquers, brilliantines, pomades and shampoos; cosmetic preparations such as creams, deodorants, hand lotions and sun screens; powders such as talcs, dusting powders, face powders and the like. When used as an olfactory component in a perfumed article, as little as 0.001% of the phenyl alkanol-containing compositions of matter of our invention and up to 3% of the phenyl alkanol-containing compositions of matter of our invention based on the ultimate end product may be used.

In addition, the perfume composition or fragrance compositions of our invention can contain a vehicle or carrier for the phenyl alkanol-containing composition of matter of our invention. The vehicle can be a liquid such as a non-toxic alcohol (e.g. 95% food grade ethanol), a non-toxic glycol (e.g. propylene glycol) or the like. The carrier can also be an absorbent solid such as a gum (e.g. gum arabic, xanthan gum or guar gum) or components for encapsulating the composition as by coacervation using gelatin or by forming a polymer wall around a liquid perfume center as by using a urea formaldehyde prepolymer to form a urea formaldehyde polymeric capsule.

The following examples are illustrative and the invention is to be considered to be restricted thereto only as indicated in the appended claims. All parts and percentages given herein are by weight unless otherwise specified.

EXAMPLE I

Preparation of 2-Methyl-Phenylethyl Alcohol

Reaction:

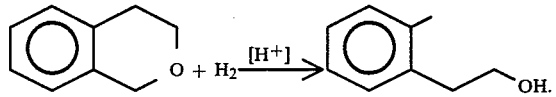

(The reactant having the structure:

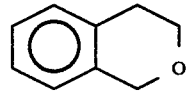

is prepared according to the reactions:

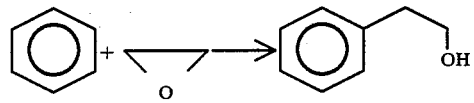

and

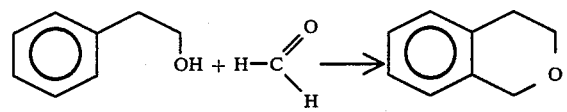

well known in the prior art.)

Into a 4 liter autoclave is placed 250 grams of the compound defined according to the structure:

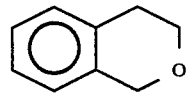

50 grams 5% palladium-on-carbon catalyst and 125 grams phosphoric acid.

Hydrogen is pumped into the autoclave after it is closed while maintaining the reaction temperature at 150°–155° C. and the pressure at 200 psig. The hydrogenation is carried out over a period of 30 hours. At the end of the 30 hour period the autoclave is opened and cooled. The resulting product is filtered and the filtrate is then subjected to fractional distillation on a 24" Goodloe column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 60/22 | 120/102 | 20 mm/3 mm | 4:1 |
| 2 | 79 | 105 | 3.0 | 4:1 |
| 3 | 79 | 105 | 3.0 | 4:1 |
| 4 | 82 | 105 | 3.0 | 4:1 |
| 5 | 85 | 105 | 3.0 | 4:1 |
| 6 | 85 | 105 | 3.0 | 4:1 |
| 7 | 90 | 105 | 3.0 | 9:1 |
| 8 | 90 | 105 | 3.0 | 9:1 |
| 9 | 85 | 105 | 3.0 | 1:1 |
| 10 | 85 | 107 | 3.0 | 2:1 |
| 11 | 85 | 107 | 3.0 | 2:1 |
| 12 | 92 | 107 | 3.0 | 2:1 |
| 13 | 85 | 107 | 3.0 | 2:1 |
| 14 | 84 | 109 | 3.0 | 2:1 |
| 15 | 85 | 109 | 3.0 | 2:1 |
| 16 | 85 | 107 | 3.0 | 2:1 |
| 17 | 84 | 110 | 3.0 | 2:1 |
| 18 | 83 | 112 | 3.0 | 2:1 |
| 19 | 81 | 130 | 3.0 | 2:1 |
| 20 | 81 | 147 | 3.0 | 2:1 |
| 21 | 34 | 200 | 3.0 | 2:1 |

Figure 1:
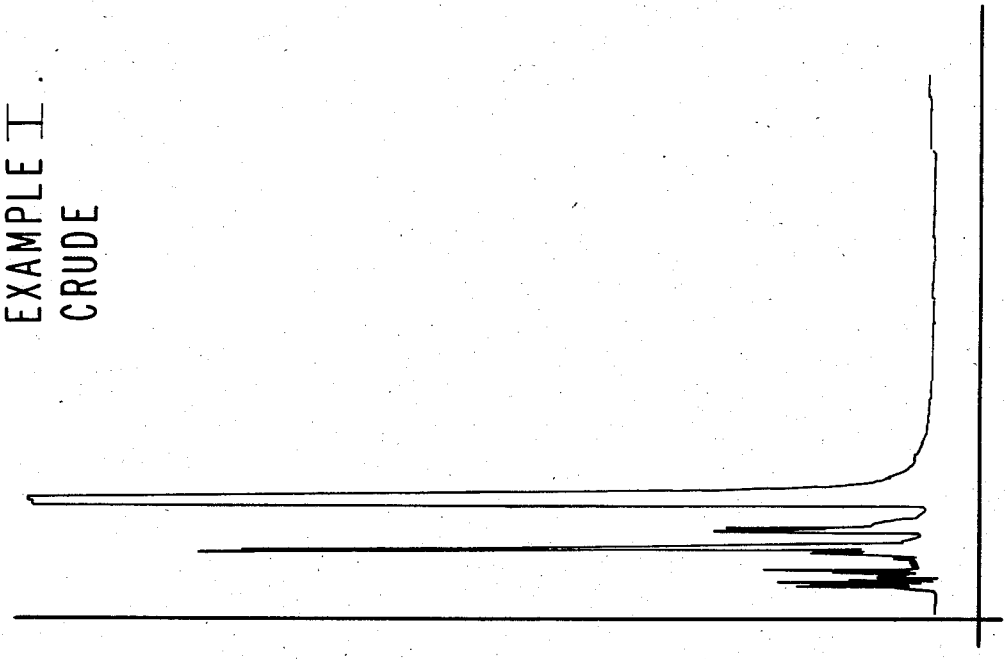
FIG. 1 is the GLC profile for the crude reaction product of Example I containing the compound having the structure.

FIG. 1 is the GLC profile for the crude reaction mass prior to distillation.

FIG. 2 is the NMR spectrum for Fraction 12 of the foregoing distillation containing substantially pure compound having the structure:

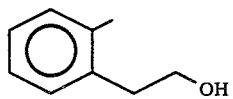

(conditions: Field strength: 100 MHz; Solvent: CFCl$_3$).

FIG. 3 is the infra-red spectrum for Fraction 12 of the foregoing distillation containing substantially pure compound having the structure:

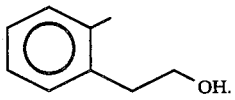

The compound having the structure:

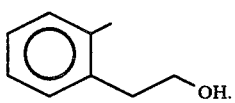

The compound having the structure:

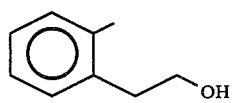

has a rosy, carnation, leafy and green aroma with balsamic and cedarwood topnotes.

EXAMPLE II

Preparation of Substantially Pure 2-Methyl Phenylethyl Alcohol

Reaction:

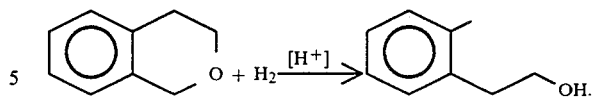

1250 Grams of isochroman having the structure:

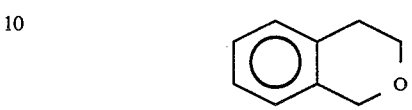

25 grams of 5% palladium-on-carbon and 12.5 grams of citric acid are placed in a 4-liter autoclave. The autoclave is sealed, heated to 150° C. and pressurized with hydrogen at 200 psig. After five hours, 12.5 grams of additional citric acid is added to the autoclave and the autoclave is resealed. The autoclave is then heated at a pressure of 200 psig and 150° C. for an additional three hours. At the end of this additional three hour period, the autoclave is opened, the contents filtered and the filtrate is distilled over 2 grams of calcium carbonate through a 24″ Goodloe column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 91/91 | 111/111 | 9.0 | 9:1 |
| 2 | 95 | 110 | 9.0 | 9:1 |
| 3 | 95 | 112 | 9.0 | 9:1 |
| 4 | 95 | 112 | 9.0 | 9:1 |
| 5 | 95 | 112 | 9.0 | 1:1 |
| 6 | 95 | 112 | 9.0 | 1:1 |
| 7 | 95 | 112 | 9.0 | 1:1 |
| 8 | 95 | 115 | 9.0 | 1:1 |
| 9 | 95 | 118 | 9.0 | 1:1 |
| 10 | 95 | 120 | 9.0 | 1:1 |
| 11 | 85 | 150 | 9.0 | 1:1 |

FIG. 4 is the GLC profile for the crude reaction product prior to distillation.

EXAMPLE III

Rose Formulation

The following mixture is prepared:

| Ingredient | Parts by Weight |
|---|---|
| Rhodinol | 270.0 |
| Nerol | 90.0 |
| Linalool | 30.0 |
| Terpineol | 30.0 |
| Phenylethyl alcohol | 12.0 |
| Terpinenol | 5.0 |
| Linalyl acetate | 1.5 |
| Citronellyl acetate | 15.0 |
| Geranyl acetate | 10.0 |
| Eugenol | 33.0 |
| Citral | 15.0 |
| Phenylethyl acetate | 20.0 |
| Rose oxide | 8.0 |
| Guaiacol | 30.0 |
| l-citronellal | 90.0 |
| Neryl acetate | 3.0 |
| Clove bud oil | 1.0 |
| Cadinene | 2.0 |
| Guaiene | 1.0 |
| Gum turpentine | 12.0 |
| Alpha-pinene | 1.0 |
| Myrcene | 5.0 |

| Ingredient | Parts by Weight |
| --- | --- |
| Limonene | 2.0 |
| p-cymene | 1.0 |

To the foregoing formulation 30 parts by weight of the pure compound defined according to the structure:

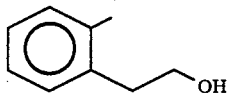

is added (Fraction 12 of the distillation product of the reaction product of Example I) or bulked Fractions 3–8 of the reaction product of Example II. The resulting mixtures have a much brighter rose, carnation, leafy and green aroma with cedarwood and balsamic topnotes and are richer on dry-out as compared with the same mixture without the substantially pure compound defined according to the structure:

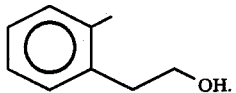

The formulation can thus be described as "intense rose, carnation, leafy and green aroma with cedarwood and balsamic topnotes".

EXAMPLE IV

Rose Formulation

The following mixture is prepared:

| Ingredient | Parts by Weight |
| --- | --- |
| Rhodinol | 270.0 |
| Nerol | 90.0 |
| Linalool | 30.0 |
| Terpineol | 30.0 |
| Phenylethyl alcohol | 12.0 |
| Terpinenol | 5.0 |
| Linalyl acetate | 1.5 |
| Citronellyl acetate | 15.0 |
| Geranyl acetate | 10.0 |
| Eugenol | 33.0 |
| Citral | 15.0 |
| Phenylethyl acetate | 20.0 |
| Rose oxide | 8.0 |
| Guaiacol | 30.0 |
| l-citronellal | 90.0 |
| Neryl acetate | 3.0 |
| Clove bud oil | 1.0 |
| Cadinene | 2.0 |
| Guaiene | 1.0 |
| Gum turpentine | 12.0 |
| Alpha-pinene | 1.0 |
| Myrcene | 5.0 |
| Limonene | 2.0 |
| p-cymene | 1.0 |

To the foregoing formulation 30 parts by weight of a mixture containing a 0.1:1:1 (mole ratio) mixture of:
(a) The compound having the structure:

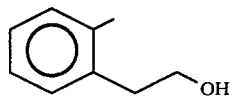

(b) 3-Methyl-1-phenyl-pentanol-5-; and
(c) Beta-damascenone is added.

The resulting mixture has a still brighter rose topnote and is fruitier and richer on dryout as compared to the same mixture as Example III. Although the resultant mixture has an intense rose, carnation, leafy and green aroma profile it is much more natural-like than the product of Example III which, in turn, is much more natural-like and richer than the product without the compound having the structure:

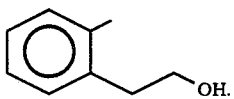

In summary, the product of this example can be described as "rose, carnation, leafy and green aroma having a fruity and rich dryout and a very intense balsamic and cedarwood topnote".

EXAMPLE V

Rose Formulation

The following mixture is prepared:

| Ingredient | Parts by Weight |
| --- | --- |
| Rhodinol | 270.0 |
| Nerol | 90.0 |
| Linalool | 30.0 |
| Terpineol | 30.0 |
| Phenylethyl alcohol | 12.0 |
| Terpinenol | 5.0 |
| Linalyl acetate | 1.5 |
| Citronellyl acetate | 15.0 |
| Geranyl acetate | 10.0 |
| Eugenol | 33.0 |
| Citral | 15.0 |
| Phenylethyl acetate | 20.0 |
| Rose oxide | 8.0 |
| Guaiacol | 30.0 |
| l-citronellal | 90.0 |
| Neryl acetate | 3.0 |
| Clove bud oil | 1.0 |
| Cadinene | 2.0 |
| Guaiene | 1.0 |
| Gum turpentine | 12.0 |
| Alpha-pinene | 1.0 |
| Myrcene | 5.0 |
| Limonene | 2.0 |
| p-cymene | 1.0 |

To the foregoing formulation 30 parts by weight of a mixture containing a 0.1:1:1 (mole ratio) mixture of:
(a) The compound having the structure:

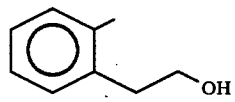

(b) 3-Methyl-1-phenyl-pentanol-5; and
(c) Trans, trans-delta damascone is added.

The resulting mixture has a still brighter rose topnote and is fruitier and richer on dryout as compared with the same mixture as Example III. Although the resultant mixture has an intense rose, carnation, leafy and green aroma profile, it much more natural-like than the product of Example III which, in turn, is much more natural-like and richer than the product without the compound having the structure:

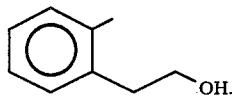

In summary, the product of this example can be described as "rose, carnation, leafy and green aroma having a fruity and rich dryout and a very intense balsamic and cedarwood topnotes".

EXAMPLE VI

Preparation of a Soap Composition

One hundred grams of soap chips are prepared according to Example V of U.S. Pat. No. 4,058,490 issued on Nov. 15, 1977, the specification for which is incorporated by reference herein as follows:

"The sodium salt of an equal mixture of $C_{10}/C_{14}$ alkane sulfonates (95% active), 40 lbs. is dissolved in a mixture of 80 lbs. of anhydrous isopropanol and 125 lbs. of deionized water at 150° F. In this mixture is dissolved 10 lbs. of partially hydrogenated coconut oil fatty acids and 15 lbs of sodium mono-$C_{14}$-alkyl maleate, and the pH of this solution is adjusted to 6.0 by the addition of a small amount of a 50% aqueous solution of NaOH. The isopropanol is distilled off and the remaining aqueous solution is drum dried. The resulting solid actives are then blended in a chip mixer with 10 lbs. water, 0.2 lbs. titanium hydroxide"

are mixed with one gram of one of the perfumery materials as set forth in Table I below until a substantially homogeneous composition is obtained. The perfumed soap composition manifests an excellent aroma as set forth in Table I below:

TABLE I

| Perfumery Product | Aroma Profile |
|---|---|
| Product having the structure: <br> 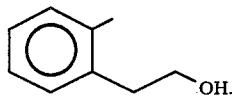 <br> produced according to either Examples I or II. | An intense rosy, carnation, leafy and green aroma with balsamic and cedarwood topnotes. |
| Perfume composition of Example III. | An intense rose, carnation, leafy and green aroma with cedarwood and balsamic topnotes. |
| Perfume composition of Example IV. | A rose, carnation, leafy and green aroma having a fruity and rich dryout and a very intense balsamic and cedarwood topnotes. |
| Perfume composition of Example V. | A rose, carnation, leafy and green aroma having a fruity and rich dryout and a very intense balsamic and cedarwood topnotes. |

TABLE I-continued

| Perfumery Product | Aroma Profile |
|---|---|

EXAMPLE VII

Preparation of a Detergent Composition

A total of 100 grams of detergent powder prepared according to U.S. Pat. No. 4,058,472, the specification for which is incorporated by reference herein and containing 5% by weight of the sodium salts of a mixture of sulfonated $C_{14}$–$C_{18}$ alkyl catechol as a surface active component, the mixture being 60 parts by weight of mono-$C_{14}$–$C_{18}$ alkyl catechol, 35% sodium tetrapyrrole phosphate, 30% of sodium carboxymethylcellulose and 7% of starch is mixed with 0.15 grams of one of the perfumery materials set forth in Table I of Example VI until a substantially homogeneous composition is obtained. This composition has an excellent aroma as set forth in Table I of Example VI.

EXAMPLE VIII

Perfumed Liquid Detergent

Concentrated liquid detergents each with an aroma as set forth in Table I of Example VI containing 0.10%, 0.15% and 0.20% of the perfumery materials of Table I of Example VI are prepared. They are prepared by adding and homogeneously mixing the appropriate quantity of perfumery material as set forth in Table I of Example VI in the liquid detergent. The detergents all possess aromas as set forth in Table I of Example VI.

EXAMPLE IX

Preparation of a Cologne and Handkerchief Perfume

The compositions as set forth in Table I of Example VI are incorporated into colognes at concentrations of 1.5%, 2.0%, 2.5%, 3.0%, 4.0% and 5.0% in 75%, 80%, 85% and 90% aqueous ethanol or diethyl phthallate and into handkerchief perfumes at concentrations of 15%, 20%, 25% and 30% (in 90% and 95% aqueous ethanol). The use of the perfumery materials of Table I of Example VI afford distinct and definitive strong aromas as set forth in Table I of Example VI in the handkerchief perfume and in the cologne.

EXAMPLE X

Preparation of a Cosmetic Powder Composition

A cosmetic powder is prepared by mixing in a ball mill 100 grams of talcum powder with 0.15 grams of the compositions of matter as set forth in Table I of Example VI supra. Each of the compositions has an excellent aroma as set forth in Table I of Example VI.

EXAMPLE XI

Utilizing the procedure of Example I at column 15 of U.S. Pat. No. 3,632,396, the specification for which is incorporated herein by reference, a non-woven cloth substrate useful as a drier added fabric softening article of manufacture is prepared wherein the substrate, the substrate coating and the outer coating and the perfuming material are as follows:

1. a water "dissolvable" paper ("Dissolvo Paper");
2. Adogen 448 (melting point about 140° F.) as the substrate coating; and 3. an outer coating having the following formulation (melting point about 150° F.):
57% C$_{20-22}$ HAPS
22% isopropyl alcohol
20% antistatic agent
1% of one of the perfumery materials set forth in Table I of Example VI giving rise to aroma nuances in the head space above a clothing batch dried using this drier-added fabric softener as set forth in Table I of Example VI supra.

Fabric softener compositions prepared as set forth above giving rise to the aroma characteristics set forth in Table I of Example VI consist of a substrate having a weight of about 3 grams per 100 square inches, a substrate coating of about 1.85 grams per 100 square inches of substrate and an outer coating of about 1.4 grams per 100 square inches of substrate thereby providing a total aromatized substrate and outer coating weight ratio of about 1:1 by weight of the substrate. As stated supra, the aromas set forth in Table I of Example VI are imparted in a pleasant manner to the head space in the drier on operation thereof using the said drier added fabric softening non-woven fabric.

What is claimed is:

1. A process for preparing a compound having the structure:

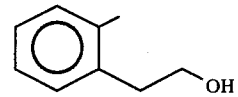

comprising the step of reacting the compound having the structure:

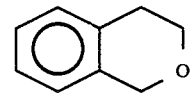

with hydrogen in the presence of a hydrogenation catalyst and an acid selection from the group consisting of mineral acids and and citric acid.

2. The process of claim 1 wherein the hydrogenation catalyst comprises palladium and the acid is a mineral acid and the mineral acid is phosphoric acid.

3. The process of claim 1 wherein the hydrogenation catalyst comprises palladium and the acid is citric acid.

* * * * *